United States Patent [19]
Grieshaber et al.

[11] Patent Number: 5,454,783
[45] Date of Patent: Oct. 3, 1995

[54] APPARATUS FOR MICROSURGICAL OPERATIONS ON THE EYE OF A LIVING BEING

[75] Inventors: Hans R. Grieshaber; Rudolf Demmerle; Urs Vogel, all of Schaffhausen, Switzerland

[73] Assignee: Grieshaber & Co AG Schaffhausen, Switzerland

[21] Appl. No.: 148,152

[22] Filed: Nov. 4, 1993

[30] Foreign Application Priority Data

Nov. 6, 1992 [CH] Switzerland ............................ 448/92
Oct. 14, 1993 [CH] Switzerland ............................ 096/93

[51] Int. Cl.⁶ .................................................. A61M 1/00
[52] U.S. Cl. .................................................. 604/30
[58] Field of Search .................... 604/30–34, 50, 604/53, 65, 66, 67, 250, 251, 253, 256; 128/DIG. 12, DIG. 13

[56] References Cited

U.S. PATENT DOCUMENTS

| | | |
|---|---|---|
| Re. 33,250 | 7/1990 | Cook . |
| 3,977,624 | 8/1976 | Leifer et al. . |
| 4,697,902 | 10/1987 | Maehara et al. . |
| 4,904,168 | 2/1990 | Cavoto et al. . |
| 4,963,131 | 10/1990 | Wortrich . |

FOREIGN PATENT DOCUMENTS

| | | |
|---|---|---|
| 0293081 | 11/1988 | European Pat. Off. . |
| 0362822 | 4/1990 | European Pat. Off. . |
| WO-A-8606964 | 12/1986 | WIPO . |

OTHER PUBLICATIONS

Computer, V. 22(10), Dec. 1989, Long Beach, US, pp. 43–54, Goodman "Knowledge–Based Computer Vision".
Software–Practice and Experience, V. 19(10), Oct. 1989, Chicester UK, pp. 979–1013, Dietrich, "TGMS: An Object–Oriented System for Programming Geometry".
Proceedings of the SPIE, V. 1659, Feb. 12, 1992, US, pp. 159–167, Haralick et al. "The Image Understanding Environment".
Intelligent Cad Oct. 6, 1987, NL, pp. 159–168, Woodbury et al, "An Approach to Geometric Reasoning".

*Primary Examiner*—John D. Yasko
*Assistant Examiner*—Manuel Mendez
*Attorney, Agent, or Firm*—Henry M. Feiereisen

[57] ABSTRACT

Apparatus for microsurgical operations on the eye of a living being includes a housing having a compartment which receives a carrier module having a first support structure for conducting a passageway for supply of an irrigation fluid to a surgical site, a second support structure spaced laterally from the first support structure for conducting a second passageway for withdrawal of material from the surgical site, and at least one catch. The compartment which is subdivided in sections by spaced partition walls houses a pump for peristaltically transporting material in the second passageway, an interrupter unit for controlling the fluid flow through the first passageway, and a pull-in and locking mechanism which is engageable with the catch for pulling the carrier module into the compartment in a snap-like manner and releasably securing the carrier module therein such that the interrupter unit is in engagement with the first passageway and the pump is in engagement with the second passageway.

14 Claims, 7 Drawing Sheets

APPARATUS FOR MICROSURGICAL OPERATIONS ON THE EYE OF A LIVING BEING

BACKGROUND OF THE INVENTION

The present invention refers to an apparatus for microsurgical operations on the eye of a living being, and in particular to an ophthalmic apparatus of the type having a housing accommodating an irrigation unit provided with a first passageway for supply of irrigation fluid to the surgical site, an aspiration unit provided with a second passageway for drawing material from the surgical site, a pump unit with a rotor cooperating with at least one circumferential, rotatably supported roller, and a carrier module releasably insertable in the housing and receiving both fluid passageways, with the carrier module being connectable with the pump unit in such a manner that the rotor peristaltically interacts via the roller with the second passageway.

European patent specification No. 0 362 882 describes a microsurgical irrigation/aspiration system which cooperates with a pump unit and includes a carrier in form of a cassette attached to the front wall of a console and retained by a pivoting latch mounted on the front wall. The carrier which receives the first and second fluid passageways has an essentially semi-circular recess for receiving the pump trait. When the carrier is installed, the rotatable rollers of the pump unit peristaltically cooperate with the fluid passageway of the aspiration unit.

Further ophthalmic devices with a pump unit and a carrier in form of a cassette are disclosed in U.S. Pat. No. 4,493,695, U.S. Pat. No. 4,735,610, U.S. Pat. No. 4,900,302, and EP-A 0 095 926.

SUMMARY OF THE INVENTION

It is an object of the present invention to provide an improved apparatus for mircosurgical operations on an eye of a living being which allows a rapid and simple insertion of the carrier module and a precise interaction of the respective fluid passageways with the pump unit.

This object, and others which will become apparent hereinafter is attained in accordance with the present invention by providing the housing with a compartment for receiving the carrier module which includes a first support structure for a first passageway through which irrigation fluid is supplied to the surgical site, and a second support structure for a second passageway through which material is withdrawn from the surgical site, with the second support structure being laterally spaced from said first support structure, and by providing the carrier module with at least one catch which upon insertion of the carrier module into the compartment cooperates with a pull-in and locking mechanism in such a manner that the first passageway engages an interrupter element and the second passageway engages the rollers of the pump unit.

The engagement of the catch by the pull-in and locking mechanism snaps the cassette-type carrier module into the compartment so as to rapidly and precisely attain an interaction between the fluid passageways of the carrier, on the one hand, and the pump unit and interrupter element in the housing compartment, on the other hand.

Suitably, the compartment is part of an exchangeable receiver and subdivided by spaced partition walls into individual sections, with the drive for the pump unit and the interrupter element being supported by a first partition wall, the locking mechanism being supported by a second partition wall and the pump unit being supported by a third partition wall. Thus, the compartment forms three functional planes accommodating distinct operational elements.

Preferably, the pull-in and locking mechanism includes a pair of pivoting spring-loaded locking levers of forked configuration to form a recess for receiving the catch of the carrier module. During installation of the carrier module in the housing compartment, the catch abuts the rear prongs of the opposing levers. Upon further advance of the carrier module into the compartment, the catch swings the levers about respective pivots until being securely retained by the forks of the levers. At this point, the rollers of the peristaltic pump engage the fluid passageway of the second support structure to allow a withdrawal of material from the surgical site to a suitable collector while the first fluid passageway is acted upon by an interrupter element by which the flow of irrigation fluid from the irrigation unit is controllable.

BRIEF DESCRIPTION OF THE DRAWING

The above and other objects, features and advantages of the present invention will now be described in more detail with reference to the accompanying drawing in which.

DETAILED DESCRIPTION OF A PREFERRED EMBODIMENT

Figure 1:
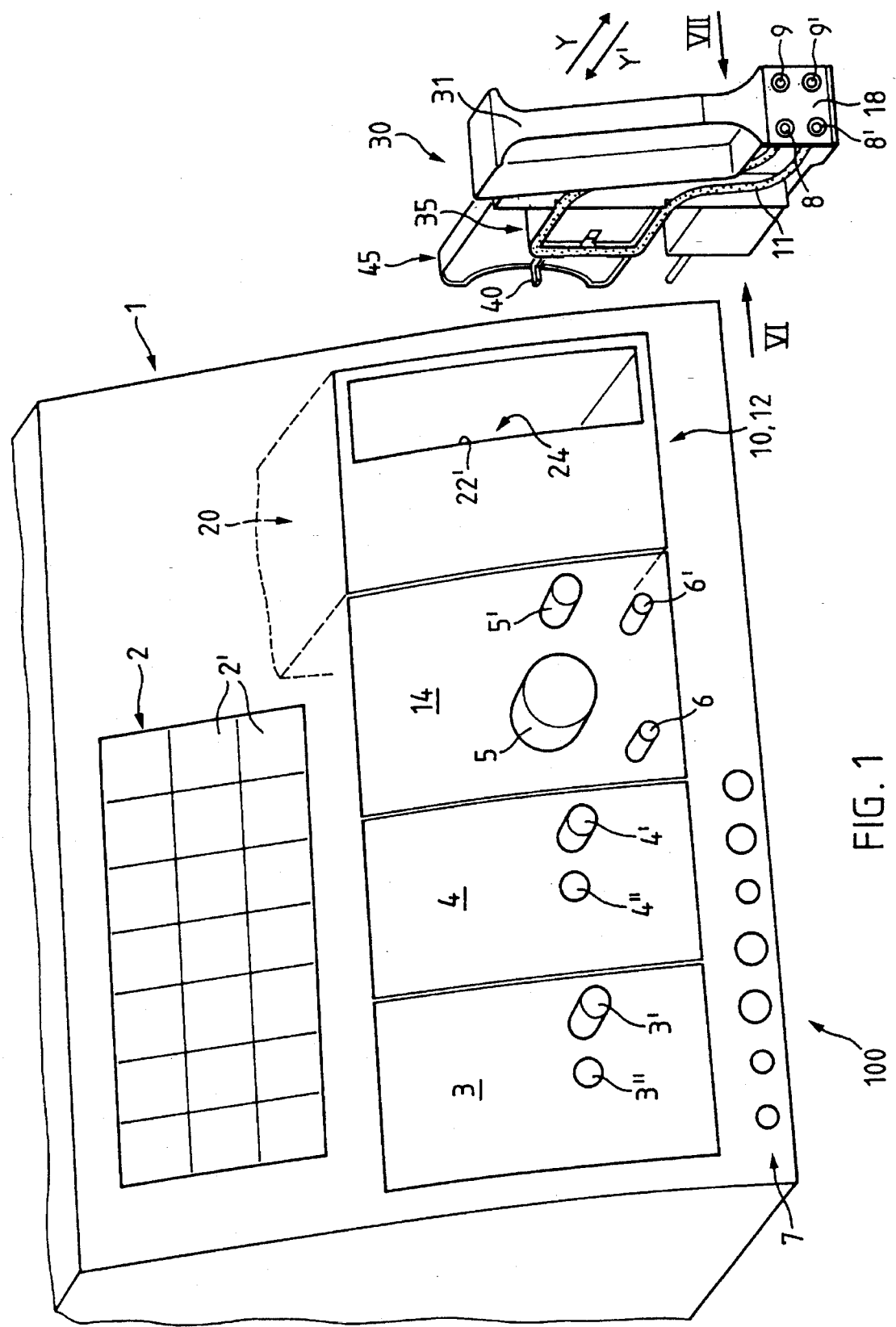
FIG. 1 is a perspective illustration of an ophthalmologic apparatus, with a cassette-type carrier module for an aspiration and irrigation unit being withdrawn from the compartment of a receiver of the ophthalmological apparatus.

Referring now to the drawing and in particular to FIG. 1, there is shown a perspective illustration of an ophthalmologic device, generally designated by reference numeral 100 for microsurgical operations on the eye of a living being. The ophthalmologic device 100 includes a housing 1 with a front console comprised of several side by side compartments receiving exchangeable functional units 3, 4, 10, 12 and 14 which are designed in form of plug-in cassettes to serve particular surgical procedures. Below the compartments, the front console of the housing 1 is provided with a multipoint connector 7 for enabling attachment of additional surgical instruments.

The functional units 3, 4 constitute illumination units for illuminating the surgical site of the eye. The structure of such illumination units 3, 4 is generally known and may include a fiber-optic cable with a light source on one end and an adapter on the other end for attachment to complimentary jacks 3" and/or 4" on the front console of housing 1. During surgical procedure the light intensity provided by the illumination units 3, 4 can be continuously controlled by adjustment knobs 3' and 4'. The fiber-optic cable together with the light source and adapter as well as much other additional apparatus such as electric circuits do not form part of the present invention and thus have been omitted from the drawing for the sake of simplicity.

The console of the housing 1 is further provided above the compartments with a display panel 2 which e.g. is subdivided into separate LCD-section 2' for indicating and controlling certain operations. The display panel 2 is part of a not shown computerized control system to provide the user with certain informations as well as to enable the user to manipulate procedures by touching respective push-button sections 2' of the panel 2 and thus to initiate a selected program which then is illuminated.

The functional unit 14 which is situated next to the illumination unit 4 is a pressure gas supply unit for feeding a pressure gas such as compressed air to the surgical site. The functional unit or pressure unit 14 includes a connector 6 for attachment of a tube and an adjustment knob 5 for controlling, preferably continuously, the supply of compressed air to the surgical site via the tube for controlling the intraocular pressure of the eye. Preferably integrated in the housing 1 and operatively connected to the pressure unit 14 is a visco-injection device (not shown) which includes a connector 6' for attachment of a tube (not shown) and an adjustment knob 5' for control purposes.

Reference numeral 24 designates a compartment which is situated next to the pressure unit 14 and is part of a receiver 20. Insertable through an opening 22' of the receiver 20 is a carrier module 30 which integrates the functional units 10, 12, representing the irrigation unit 10 and the aspiration unit 12. The carrier module 30 is depicted in FIG. 1 in a withdrawn position and includes a front panel 18 provided with spaced connectors 8, 8' and 9, 9' for attachment of respective supply and discharge lines of the aspiration and irrigation system.

As will be appreciated from the foregoing, the receiver 20 is releasably secured to the housing 1. However, it is certainly also within the scope of the present invention to integrate the compartment for receiving the carrier module 30 and the respective operational elements in the housing 1.

As illustrated in FIG. 1, the carrier module 30 is insertable within the receiver 20 in a direction indicated by arrow Y' and can be withdrawn from the receiver 20 in direction of arrow Y. In order to facilitate the installation, the carrier module 30 is provided with a handpiece 31, with the front panel 18 including the spaced connectors 8, 8' and 9, 9' being arranged beneath the handpiece 31. The carrier module 30 has a first support structure, generally designated by reference numeral 35 for accommodating a passageway or tubing 11 to supply an irrigation fluid, such as saline solution, to the surgical site. Laterally spaced from the first support structure 35, the carrier module 30 includes a second support structure which is generally designated by reference numeral 45 and accommodates a passageway or tubing 13 (FIG. 5) for withdrawing and removing material (tissue and/or fluid) from the surgical site. The second support structure 45 further includes a catch 40 at the side facing the first support structure 35 for cooperation with a pull-in and locking mechanism 60 (FIG. 3) which is mounted within the receiver 20, as will be described furtherbelow.

Figure 2:
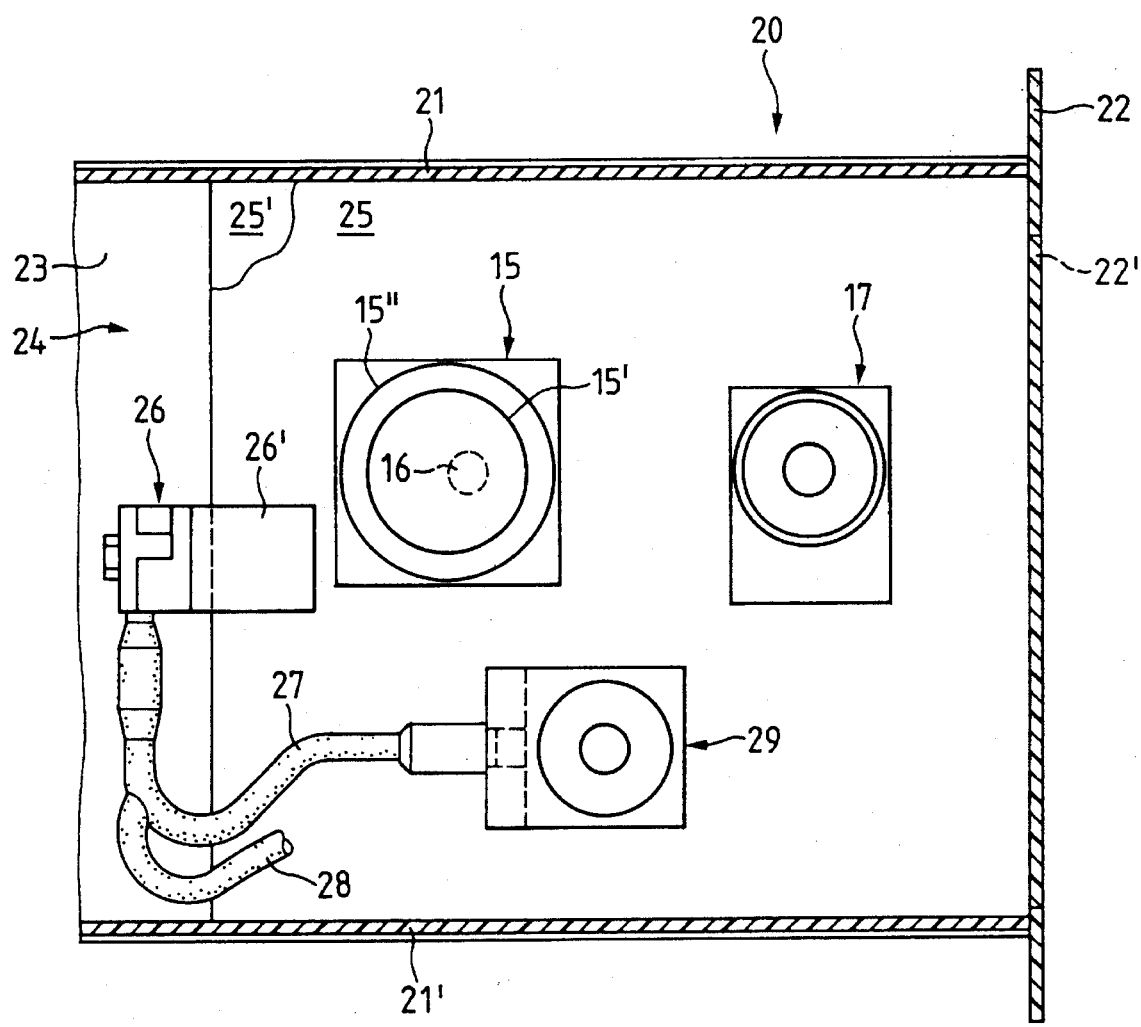
FIG. 2 is an enlarged, partly cross-sectional view of the receiver for the carrier module, illustrating in detail a first functional plane for arrangement of respective operational elements.

Turning now to FIG. 2, there is shown an enlarged, partly sectional view of the receiver 20 which is essentially of box-shaped configuration with a top plate 21 and a bottom plate 21', two side walls 23, 23' (FIG. 9), a front plate 22 in which the opening 22' is formed and a not shown rear wall. Top plate 21, bottom plate 21' and side walls 23, 23' as well as front plate 22 generally define the compartment 24 for receiving the carrier module 30 which is inserted through opening 22'.

Figure 4:
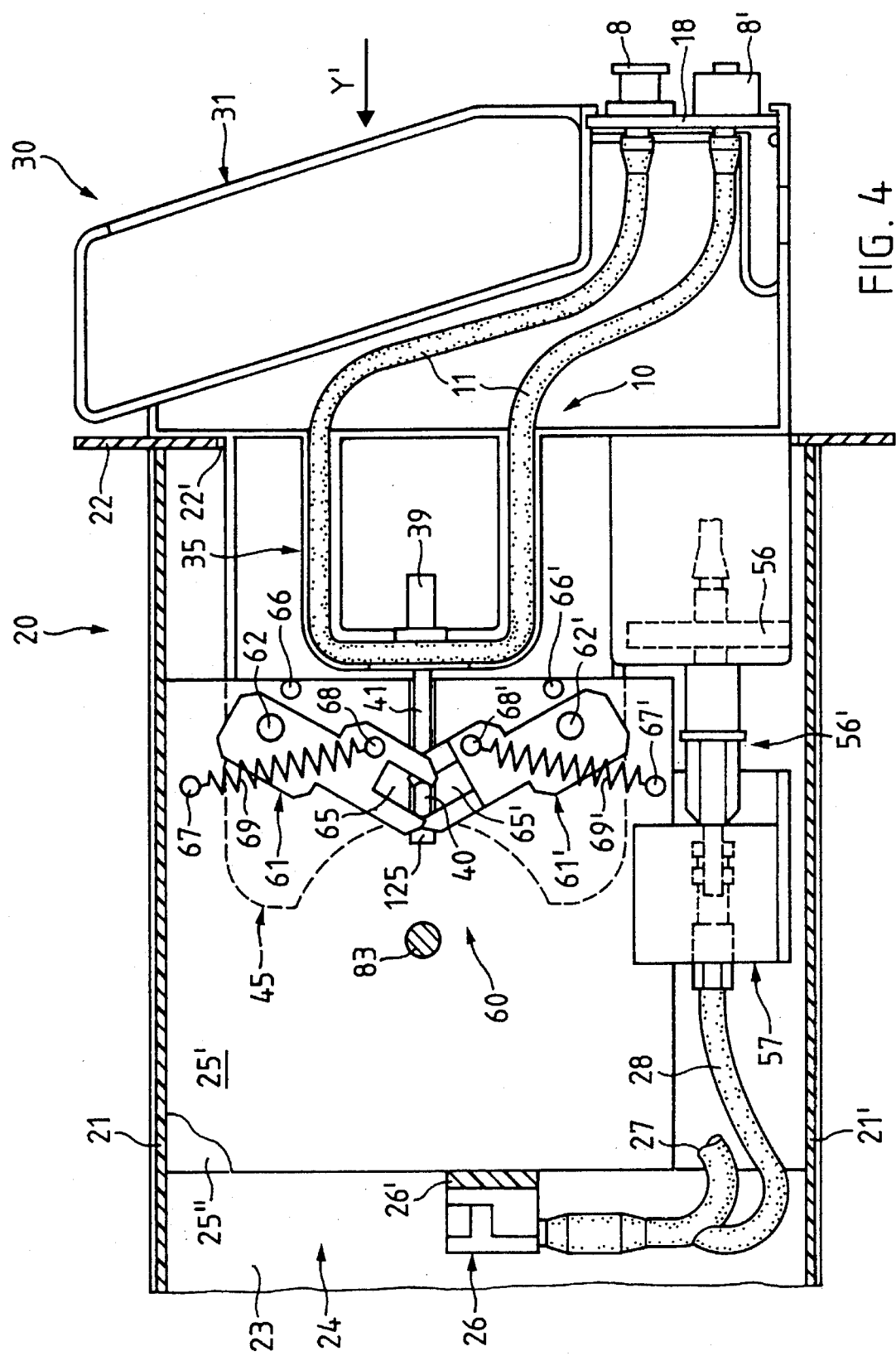
FIG. 4 is an enlarged, partly cross-sectional view of the receiver according to FIG. 3, with the carrier module occupying its fully installed position within the compartment of the receiver.

The compartment 24 of the receiver 20 is subdivided in three functional planes by respective flat partition walls. A first partition wall 25 extends between the top plate 21 and the bottom plate 21' and, as shown in particular in FIG. 9 which illustrates a sectional top view of the receiver 20, supports a drive unit, generally designated by reference numeral 15 for operating a pump, which is illustrated in detail in FIG. 5 and designated by reference numeral 70. The drive unit 15 is provided with a motor 15', a gear box 15" and a drive shaft 16 for connection to the pump unit 70. Further mounted to the partition wall 25 is a solenoid valve 17 which is part of an interrupter unit with a squeeze element 17' for controlling the flow of fluid through passageway 11 of the irrigation unit 10. A vent valve 29 is also attached to the partition wall 25 for allowing gaseous fluid withdrawn from the eye to be discharged via a conduit 27, with the pressure in conduit 27 being measured by a pressure gage 26. Conduit 28 which is shown in FIG. 2 branching off conduit 27 is in communication with an adapter 57 for releasable connection with the tubing 13 (FIG. 4).

The operational elements 15, 17, 26 and 29 form together with the partition wall 25 the first functional plane.

Figure 9:
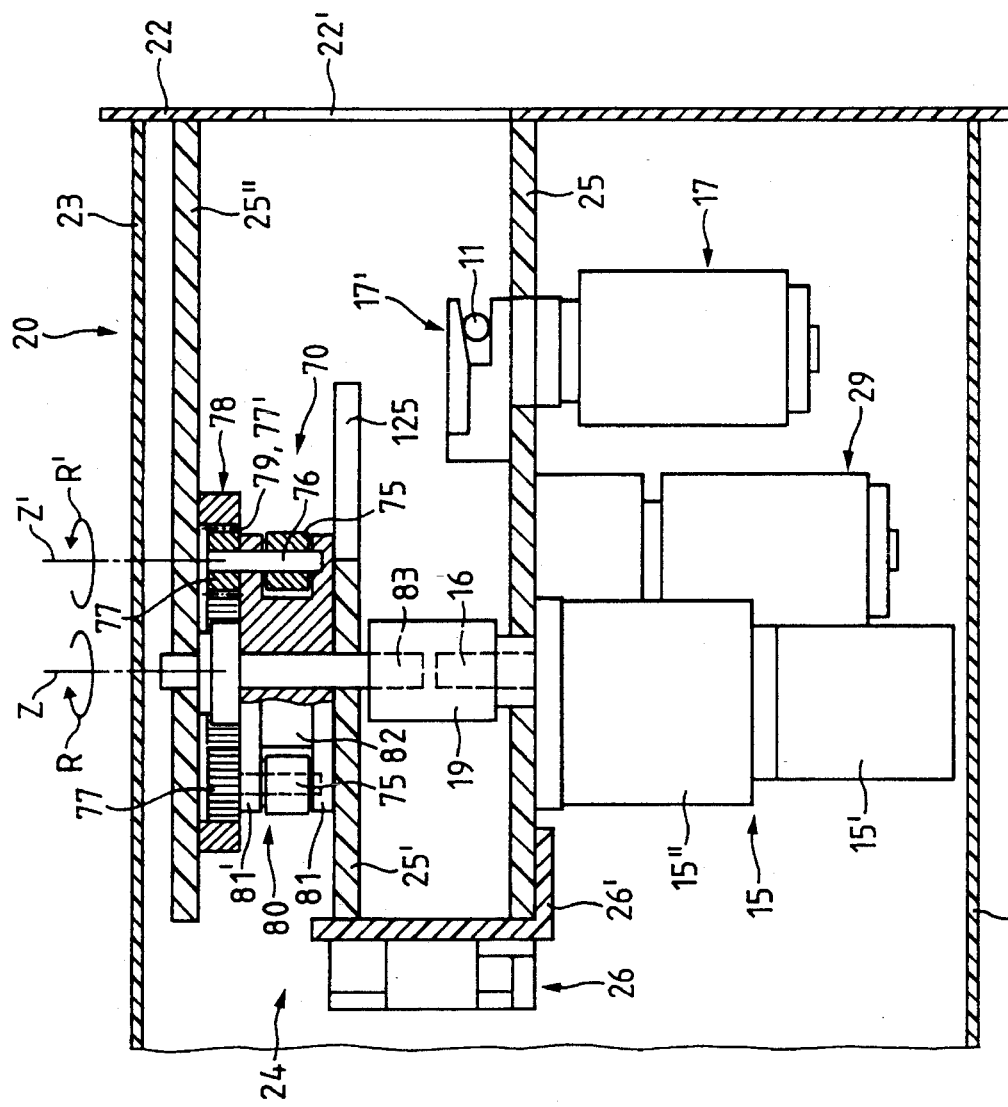
FIG. 9 is a partly sectional top view of the receiver illustrating the three functional planes with their respective operational elements.

Spaced in parallel relationship from the partition wall 25 is a second partition wall 25' which supports the pull-in and locking mechanism 60, as will be described in more detail in connection with FIG. 3 and receives one end of an L-shaped mounting 26', as best seen in FIG. 9. The mounting 26' extends between the partition walls 25, 25' for support of the pressure gage 26. A third partition wall 25" is spaced in parallel relationship from the partition wall 25' for support of the pump unit 70.

Figure 3:
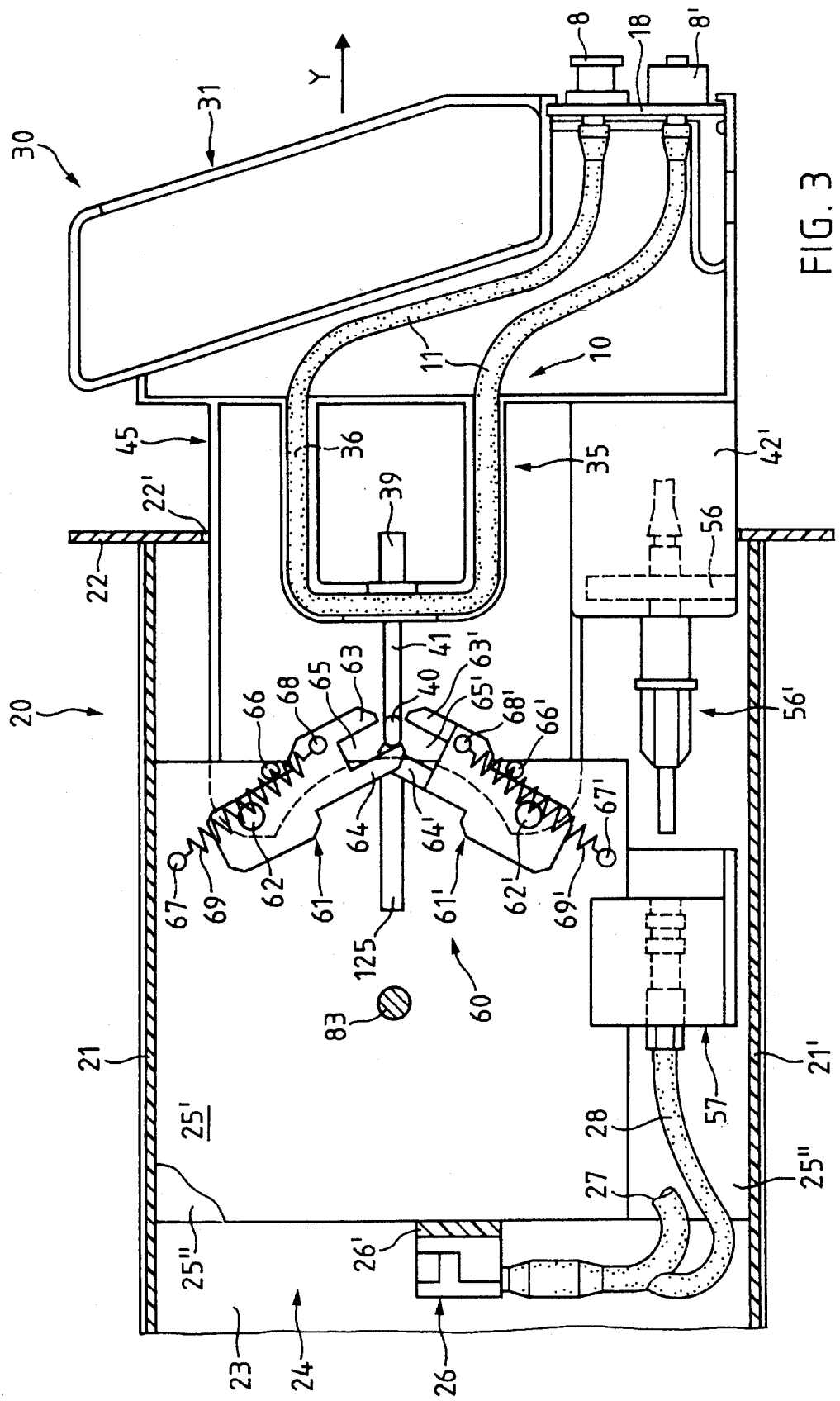
FIG. 3 is an enlarged, partly cross-sectional view of the receiver, illustrating in detail a second functional plane for accommodating the pull-in and locking mechanism for a partly installed carrier module.

Turning now to FIG. 3, there is shown an enlarged, partly sectional view of the receiver 20, with the carrier module 30 occupying an intermediate position in which the carrier module 30 is partly withdrawn from the compartment 24, as indicated by arrow Y. The tubing 11 of the first support structure 35 of the carrier module 30 is conducted in a channel 36 which will be described in more detail with reference to FIG. 6. As stated earlier, the pull-in and locking mechanism 60 is mounted to the partition wall 25' and includes a pair of opposing locking levers 61, 61', with one end shaped in form of a fork with prongs 63, 64; 63',64' and recess 65, 65' for gasping the catch 40 of the carrier module 30 With their other end, the locking levers 61, 61' are swingably mounted in opposition to the return force of tensile members 69, 69' about pivots 62, 62' which are secured in the partition wall 25'. Preferably, the tensile members 69, 69' are helical springs which respectively extend between abutments 67, 67', secured to the partition wall 25' and abutments 68, 68' mounted on the levers 61, 61'.

In the illustration of FIG. 3, the locking levers 61, 61' occupy a release position in which the catch 40 is released from the locking levers 61, 61' when withdrawing the carrier module 30 from the compartment 24 of the receiver 20 or acts upon the levers 61, 61' for pulling or snatching the carrier module 30 completely into the compartment 24, as shown in FIG. 4. Upon entering the compartment 24, the catch 40 of carrier module 30 impacts the superimposed rear prongs 64, 64' of the locking levers 61, 61'. In alignment with the catch 40, the partition wall 25' is provided with an axial slot 125 to allow a further advance of the carrier module 30 in direction of arrow Y'. During advance of the carrier module 30, the locking levers 61, 61' are forced by the catch 40 to swing about the pivots 62, 62', with the catch 40 entering the slot 125. At the same time the helical springs 69, 69' swing about the abutment 67, 67' and are tensed. Upon reaching and exceeding a dead center position of the locking levers 61, 61' the return force of the helical springs 69, 69' pulls the carrier module 30 in a snap-like manner into the compartment 24 of the receiver 20 to occupy the installation position as shown in FIG. 4. In this position of the locking levers 61, 61' the catch 40 of the carrier module 30 is securely retained in the recesses 65, 65' of the locking levers 61, 61' since the prongs 63, 64 of the locking lever 61 overlap the prongs 63', 64' of the locking lever 61'

At withdrawal of the carrier module 30 from the receiver 20 in direction of arrow Y, the catch 40 pushes against the other prongs 63, 63' to swing the locking levers 61, 61' and the helical springs 69, 69' into the release position in which the prong 63 of lever 61 is spaced from the opposing prong 63' of lever 61' to define a gap of sufficient dimension to allow a passage of the catch 40 upon further retraction of the carrier module 30, as shown in FIG. 3. Suitably, stops 66, 66' are secured to the partition wall 25' in the path of movement of the levers 61, 61' to limit their swinging motion.

Figure 5:
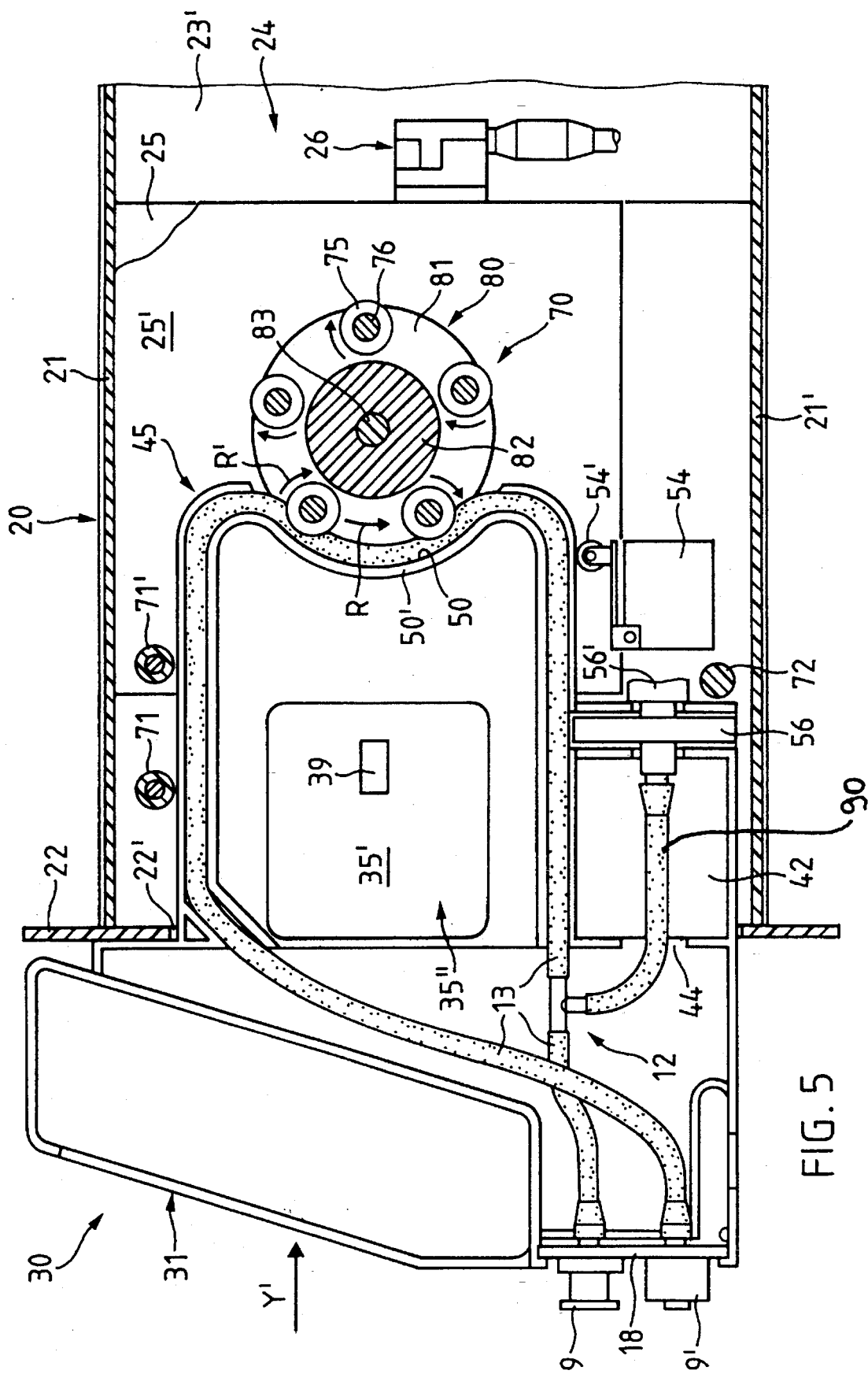
FIG. 5 is an enlarged, partly sectional view of the receiver, illustrating a third functional plane for arrangement of a schematically illustrated pump unit.

The slot 125 in the partition wall 25' not only allows the advance of the catch 90 but also guides the catch 40 precisely during insertion of the carrier module 30 into the receiver 20 so that the carrier module 30 is effectively and rapidly installed and accurately positioned in the compartment 24 of the receiver 20 relative to the pull-in and locking mechanism 60 and for operative connection of the tubing 13 of the second support structure 45 of the carrier module 30 with the pump unit 70, as will be now be described with reference to FIG. 5.

FIG. 5 is an enlarged, partly sectional view of the receiver 20, illustrating in particular the partition wall 25" for supporting the pump unit 70 by which material is forced through tubing 13 of the second support structure 45 of the carrier module 30. In order to further improve the precise guidance of the support structure 45 relative to the pump unit 70 and to prevent a canting of the carrier module 30 during installation in the receiver 20, the partition wall 25" carries spaced rollers 71, 71' and a stop member 72.

The pump 70 is driven by the drive unit 15 via shafts 16 and 83 and interposed coupling 19 (FIG. 9) and includes a rotor 80 which is securely mounted on the shaft 83 for rotation in the direction of arrow R. Evenly arranged about the circumference of the rotor 80 are rollers 75. In the non-limiting example of FIG. 5, the rotor 80 is provided with five circumferential rollers 75 in order to ensure that at least two rollers 75 are engaged in each position of the rotor 80 with the tubing 13 of the second support structure 45. Each roller 75 is rotatably supported on a shaft 76 and rotatable in opposite direction to the rotor 80 as indicated by arrow R'.

During rotation of the rotor 80, the rollers 75 advance the fluid in tubing 13 and thus enable an optimum operation of the peristaltically pumping rotor 80. Suitably, the tubing 13 is guided along an arcuate path 50 which complements the configuration of the rotor 80 in order to avoid tensile forces to act on and stretch the tubing 13. Thus, during insertion of the carrier module 30 in the compartment 24 of the receiver 20, the support structure 45 is precisely guided and positioned relative to the pump unit 70 by the catch 40 and slot 125, on the one hand, and the rollers 71, 71', on the other hand.

Further mounted to the partition wall 25" is a switch 54 which is provided with a tracer 54' for sensing an installed carrier module 30. When the carrier module 30 is installed in the receiver 20, the tracer 54' senses the end position of the support structure 45 and the switch 54 sends a signal to actuate the pump unit 70.

Figure 6:
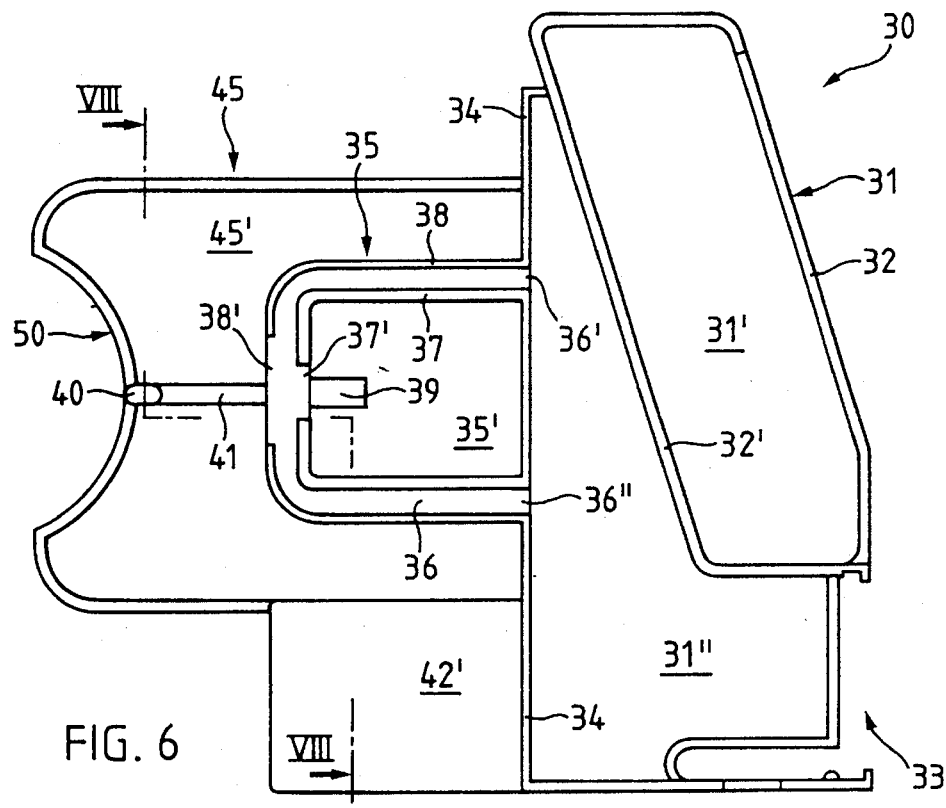
FIG. 6 is an enlarged side view of the carrier module in direction of arrow VI in FIG. 1, illustrating in detail the fluid passageway for the irrigation unit.

Referring now to FIG. 6, there is shown an enlarged side view of the carrier module 60 viewed in direction of arrow VI in FIG. 1. Both support structures 35, 45 of the carrier module 30 are separated from the handpiece 31 by a vertical wall 34. The handpiece 31 is of generally rectangular shape with two parallel plates 32, 32' and an interposed reinforcement plate 31' for stabilization. A second reinforcement plate 31" is arranged between the vertical wall 34 and the plate 32'. The front of the handpiece 31 is further provided with a recess 33 for attachment of the front panel 18 with the connectors 8, 8' and 9, 9'.

The first support structure 35 which is attached to the vertical wall 34 has a bottom plate 35' for defining a space 35". Connected to the outer perimeter of the bottom plate 35' is a complementary outer C-shaped guide 38 and spaced thereto in parallel relationship an inner C-shaped guide element 37 for forming the channel 36 in which the tubing 11 of the irrigation unit 10 is guided, as also shown in FIGS. 3 and 4. At the side facing the arcuate path 50, each of the guide elements 37, 38 is provided with a recess 37', 38' and the bottom plate 35' is provided with an opening 39 for receiving the interrupter element 17' by which the fluid flow through tubing 11 is controlled. The squeeze or interrupter element 17' of the solenoid valve 17 clamps and opens the elastic tubing 11 depending on the control of the solenoid valve 17. Suitably, the tubing 11 is pressed against an abutment (not shown) during clamping action of the interrupter element 17'. In order to allow an engagement with the tubing 11, the interrupter element 17' projects through opening 39 in the bottom plate 35', with the recesses 37', 38' permitting a lowering of the squeeze element 17' toward the tubing 11 to clamp or squeeze the tubing 11. The vertical wall 34 is further provided in the area of the channel 36 with recesses 36', 36" for ensuring an unobstructed and straight exit of the tubing 11 toward connectors 8, 8'.

FIG. 6 further shows the arrangement of the support structure 45 with a bottom plate 45' for supporting the catch 40. Extending from the catch 40 in direction toward the first support structure 35 is a guide rib 41. Arranged laterally of the bottom plate 45' is a space 42 for receiving a tube 90 which branches off tubing 13 and is connected to a coupler 6' with filter 56 (FIG. 5). As shown in FIGS. 3 and 4, upon installation of the carrier module 30 in the receiver 20, the coupler 56 is inserted in a complementary adapter 57 which is connected to tube 28. In this manner, gaseous fluid can escape through vent valve 29 via tube 27 after passing through the filter 56.

Figure 7:
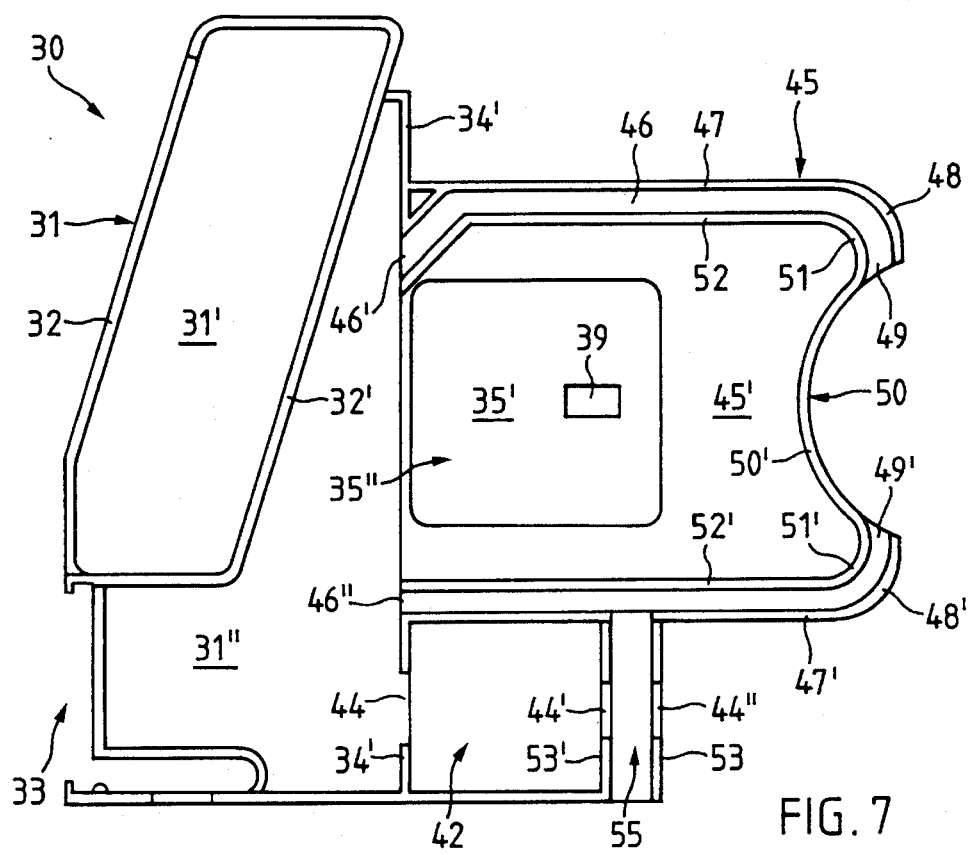
FIG. 7 is an enlarged side view of the carrier module in direction of arrow VII in FIG. 1 and illustrating a second fluid passageway for the aspiration unit.

FIG. 7 illustrates an enlarged side view of the second support structure 45 of the carrier module 30, with a vertical wall 34' separating the support structure 45 from the handpiece 31. Mounted to the outer periphery of the bottom plate 45' is an outer guide 47, 47' and spaced thereto in parallel relationship an inner guide 52, 52' for forming a channel 46 in which the tubing 13 is conducted. Connected to both outer guides 47, 47' is an arched section 48, 48' and connected to the inner guide 52, 52' is an arched section 51, 51'. The channel 46 is provided at the side facing the arcuate path 50 with recesses 49, 49' and the vertical wall 34' is provided with respective bores 46', 46" for allowing an unobstructed guidance of the tubing 13 from the connector 9 to the connector 9' via the channel 46. The arched sections 48, 51 and 48', 51' formed in succession of the straight guides 47, 52; 47', 52' on the bottom plate 45' allow guidance of the tube 13 without any buckling along the arcuate path 50.

At the side opposite to the vertical wall 34' and next to the space 42 is a chamber 55 which is defined by two spaced side walls 53, 53' and receives the filter 56 which is supported in suitable bores 44, 44' in the side walls 53, 53'. The wall 34' also includes a bore 44 for passage of tube 90, as shown in FIG. 5.

Figure 8:
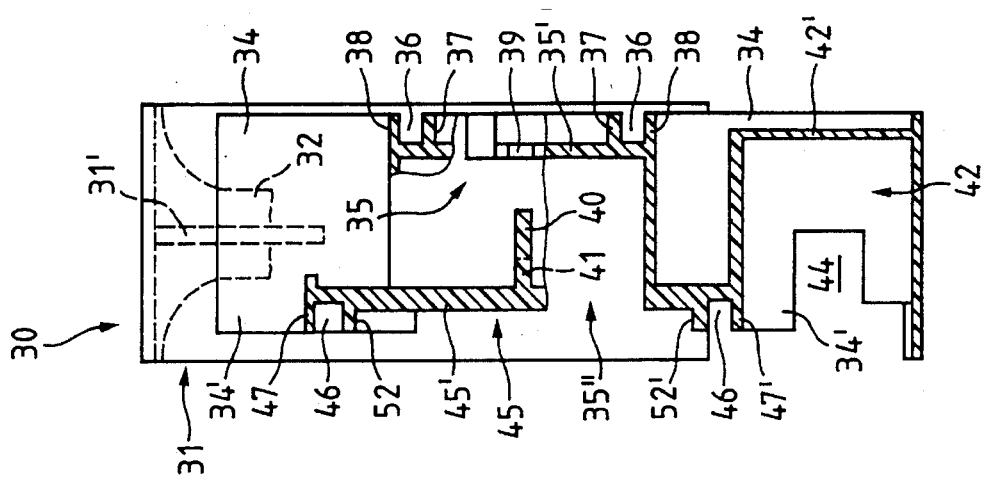
FIG. 8 is a sectional view of the carrier module taken along the line VIII—VIII in FIG. 6.

FIG. 8 is a sectional view of the carrier module 30 taken along the line VIII—VIII in FIG. 6 and illustrates the parallel arrangement of the first and second support structures 35, 45 transversely to the direction of insertion Y'. Arranged on the bottom plate 35' are the spaced guides 37, 38 which form the channel 36 for the tubing 11. The first support structure 35 has a cavity 35" which is open in direction towards the second support structure 45. Also illustrated in FIG. 8 is the bottom plate 45' of the second support structure 45 for supporting the guides 47, 52 and 47', 52' which form the channel 46 for the tubing 13. Also recognizable is in the lower area the space 42 which is defined by the wall 42', and the bore 44 in the vertical wall 34'.

Referring now to FIG. 9, there is shown a partly sectional top view of the receiver 20 illustrating the three functional planes with their respective operational elements, and in particular depicting the connection between the drive unit 15 and the pump unit 70. As stated earlier, the pump unit 70 is mounted to the partition wall 25" at the side facing the partition wall 25'. Further attached to the partition wall 25" is a gear rim 78 which includes an internal toothing 79 in mesh with the external toothing 77' of several circumferentially spaced pinions 77 which are respectively connected to the rollers 75 via the shafts 76 so as to provide the operative connection between the drive unit 15 and the rotor 80.

As further shown in FIG. 9, the rotor 80 includes two parallel disks 81, 81' which are arranged at a distance from each other by a cylindrical spacer 82. The rollers 75 are arranged between these disks 81, 81' and mounted to the shafts 76. During a rotation of the motor 80 about the axis Z in direction of arrow R, the rollers 75 rotate about the axis Z' in direction of arrow R' opposite to the rotor 80.

While the invention has been illustrated and described as embodied in an apparatus for microsurgical operations on the eye of a living being, it is not intended to be limited to the details shown since various modifications and structural changes may be made without departing in any way from the spirit of the present invention.

What is claimed as new and desired to be protected by Letters Patent is set forth in the appended claims:

1. Apparatus for microsurgical operations on the eye of a living being, comprising:

a housing having a compartment;

a carrier module insertable in said compartment and including a first support structure conducting a first passageway for supply of an irrigation fluid to a surgical site and a second support structure spaced laterally from said first support structure and conducting a second passageway for withdrawal of material from the surgical site;

pump means accommodated in said housing for peristaltically transporting material in said second passageway;

fluid control means cooperating with said first passageway for selectively interrupting a fluid flow through said first passageway; and pull-in and locking means for releasably securing said carrier module in said compartment in such a manner that in operational position of said carrier module said fluid control means is in engagement with said first passageway and said pump means is in engagement with said second passageway, said pull-in and locking means including a catch secured to said second support structure of said carrier module at one end facing said compartment of said housing, and a locking member arranged inside said compartment and having one end configured to receive said catch and another end swingably mounted for rotation of said locking member between a receiving position in which said one end receives said catch and a fixing position in which said locking member turns about its pivot axis to automatically pull said catch with said carrier module into said compartment for securely aligning said carrier module in the operational position in said compartment.

2. Apparatus as defined in claim 1, and further comprising a drive unit for driving said pump means, said compartment being subdivided by spaced partition walls into individual sections, at least said drive unit and said fluid control means being secured to a first one of said partition walls, said pull-in and locking means being secured to a second one of said partition walls, and said pump means being secured to a third one of said partition walls.

3. Apparatus as defined in claim 2 wherein said locking member of said pull-in and locking means includes a pair of pivoting locking spring-loaded levers having one end mounted to said second partition wall at the side facing said first partition wall and another end engageable with said catch, each of said locking levers being of forked configuration to form a recess for receiving said catch.

4. Apparatus as defined in claim 3 wherein said second partition wall includes stop means for restricting a swinging motion of said locking levers during withdrawal of said carrier module from said compartment.

5. Apparatus as defined in claim 3 wherein said second partition wall includes an axial slot, said catch being guided in said axial slot during insertion of said carrier module in said compartment.

6. Apparatus as defined in claim 2 wherein said pump means includes a rotor with a plurality of circumferentially spaced rollers, with at least two rollers acting on said second passageway during rotation of said rotor.

7. Apparatus as defined in claim 6 wherein said pump means is mounted to said third partition wall at the side facing said second partition wall, said rotor being configured in form of a pair of disks distanced from each other by a spacer, with said rollers being rotatable in opposite direction to said rotor.

8. Apparatus as defined in claim 7 wherein each of said rollers is rotatably supported about a shaft carrying a pinion, said drive unit including a gear rim mounted to said third partition wall and including an internal toothing in mesh with each pinion.

9. Apparatus as defined in claim 1 wherein said first support structure includes a channel for receiving said first passageway and said second support structure includes a channel at a side facing away from said channel of said first support structure for receiving said second passageway.

10. Apparatus as defined in claim 9 wherein said first support structure includes a C-shaped guide for defining said channel and said second support structure includes a guide element with an arcuate path and essentially parallel arched sections for defining said channel of said second support structure.

11. Apparatus as defined in claim 10 wherein said second support structure is configured essentially in form of a flat plate having one end provided with said arcuate path for engagement of said pump means with said second passageway, with said catch being mounted onto said second support structure at a side facing said first support structure and connected to a guide rib formed on said plate.

12. Apparatus as defined in claim 11, and further comprising a filter for cooperation with said second passageway, said plate of said second support structure including a chamber for receiving said filter.

13. Apparatus as defined in claim 1 wherein said carrier includes a handpiece made of plastic material and having one end formed with a recess for attachment of a front panel with connectors.

14. The apparatus as defined in claim 1 wherein said carrier module has a narrow side, said carrier module being inserted with its narrow side into said compartment.

* * * * *